United States Patent [19]

Harper

[11] Patent Number: 5,320,812

[45] Date of Patent: Jun. 14, 1994

[54] CLOT ACTIVATING POLYELECTROLYTE COMPLEX AND BLOOD COLLECTION ASSEMBLY CONTAINING SAME

[75] Inventor: Garry R. Harper, Raleigh, N.C.

[73] Assignee: Becton, Dickinson and Company, N.J.

[21] Appl. No.: 130,801

[22] Filed: Oct. 4, 1993

[51] Int. Cl.$^5$ ............... G01N 3/00; G01N 33/48; G01N 33/86

[52] U.S. Cl. ............... 422/102; 422/73; 422/101; 436/69; 428/407; 428/509; 604/416

[58] Field of Search ............... 422/73, 101, 102; 436/69; 428/407, 509, 510; 604/416

[56] References Cited

U.S. PATENT DOCUMENTS

| | | | |
|---|---|---|---|
| 3,554,985 | 1/1971 | Fields et al. | 260/78.5 |
| 3,555,001 | 1/1971 | Wallis et al. | 260/112 |
| 3,655,509 | 4/1972 | Fields et al. | 195/1.5 |
| 4,153,739 | 5/1979 | Kessler | 428/417 X |
| 4,189,382 | 2/1980 | Zine, Jr. | 210/46 |
| 4,257,886 | 3/1981 | Kessler | 210/516 |
| 4,420,517 | 12/1983 | Ali | 604/403 X |
| 4,579,828 | 4/1986 | Ali | 422/102 X |
| 5,246,666 | 9/1993 | Vogler et al. | 422/102 X |
| 5,257,633 | 11/1993 | Vogler et al. | 128/763 |

OTHER PUBLICATIONS

Ito, et al., "In Vivo An In Vitro Blood Compatibility of Polyelectrolyte Complexes Formem Between Cellulose derivatives", J. Appl. Polymer Sci. 32, 1986 3413-3421.
Kikuchi, et al., "Properties of Polyelectrolyte Complexes Consisting of . . . ", Bulletin of The Chemical Society of Japan, 54(8), (1981), 2549-2550.
1991-1992 Scientific Products General Catalog, Baxter.
Kikuchi et al., "Properties of Polyelectrolyte Complexes Consisting of [2-(Diethylamino)-ethyl]dextran Hydrochloride, Carboxymethyldextran and Sodium Dextron Sulfate for Clot Formation in Vitro.", Bulletin of the Chemical Society of Japan, 55, 2307-8, 1982.

Primary Examiner—James C. Housel
Assistant Examiner—Milton I. Cano
Attorney, Agent, or Firm—Richard E. Brown

[57] ABSTRACT

An additive for a blood collection container is a polyelectrolyte complex having a surface charge which activates clotting of a blood sample in the container. A preferred additive is a crosslinked carboxylated cellulose having a negative charge. The invention includes a blood collection tube having a puncturable stopper in an open end and the additive of the invention deployed therein.

10 Claims, 5 Drawing Sheets

CLOT ACTIVATING POLYELECTROLYTE COMPLEX AND BLOOD COLLECTION ASSEMBLY CONTAINING SAME

BACKGROUND OF THE INVENTION

1. Field of the Invention

This invention relates to blood collection and, more particularly, relates to a plastic blood sample collection assembly.

2. Background

Blood samples are routinely taken in glass evacuated tubes. One end of a double-ended needle is inserted into a patient's vein. The other end of the needle then punctures a stopper covering the open end of the tube so that the vacuum in the tube draws the blood sample through the needle into the tube. Using this technique, a plurality of samples can be taken using a single needle puncture of the skin.

Plastic tubes have also been proposed for blood collection. Plastic offers a number of advantages over glass such as lower breakage, less weight in shipment, and easier disposal by incineration.

Blood collected in evacuated tubes often must be clotted prior to clinical examination. It is desirable to form a dense clot as rapidly and completely a possible to facilitate clean separation of the clot from the serum layer by centrifugation. To achieve this end, both plastic and glass blood collection tubes frequently employ a clot activator.

Practically all commercial blood collection tubes include particulate activators which lead to dense, crosslinked clots that cleanly separate from the serum in a hematological centrifuge. Clot formation, however, is relatively slow, particularly in plastic, and about 30–60 minutes are required prior to centrifugation. Typical particulate activators used commercially are silica impregnated in fabric, silica particles in small plastic cups or silicate particles applied to the tube wall in polyvinylpyrrolidone (PVP). When blood enters a tube containing silicate-PVP, the PVP dissolves and the silicate particles are released. The PVP enters both the serum and the clot and may interfere with chemical or hematological assays and may foul automated and/or optical instruments.

There is a need in the art for a clot activator which rapidly forms a dense clot which separates cleanly from the serum on centrifugation without contaminating the serum with soluble chemicals. The present invention is directed to fulfilling this need.

SUMMARY OF THE INVENTION

One aspect of the present invention is a crosslinked insoluble polyelectrolyte complex (PEC) clot activating additive for a blood collection assembly. The PEC is a polyionic polymer having a surface charge which enhances the rate of clotting of a blood sample.

A first embodiment of the additive is a gel bead formed by crosslinking a polymer having carboxyl groups and carboxylate anions which provide a negative surface charge. A second embodiment of the additive is a multilayered structure having a crosslinked core, one or more laminated layers thereon, and a charge on the surface layer. The preferred crosslinking agent is a divalent or polyvalent metal ion.

Another aspect of the invention is a blood collection assembly which includes an evacuated tube closed with a puncturable septum and having the additive of the invention therein.

Thus the additive has a surface chemistry which activates clotting of a blood sample. Because it is insoluble in an aqueous medium, the additive, after triggering the clotting mechanism, is centrifuged along with the clot and is removed from the serum layer. The additive may be produced in any desired shape, density or surface chemistry so that blood samples of any size can be processed rapidly with minimal effect on any blood components intended for analysis.

DETAILED DESCRIPTION

While this invention is satisfied by embodiments in many different forms, there will herein be described in detail preferred embodiments of the invention with the understanding that the present disclosure is to be considered as exemplary of the principles of the invention and is not intended to limit the invention to the embodiments illustrated and described. The scope of the invention will be measured by the appended claims and their equivalents.

The blood collection assembly of the invention may include any container having the PEC activator of the invention therein. Suitable containers are, for example bottles, vials, flasks and the like, preferably tubes. The invention will henceforth be described in terms of the preferred tube.

The tube may preferably be combined with a puncturable septum over the open end and may be evacuated. Evacuated tubes for blood collection are standard in the art as, for example, VACUTAINER TM brand tubes (Becton, Dickinson and Company).

Figure 1:
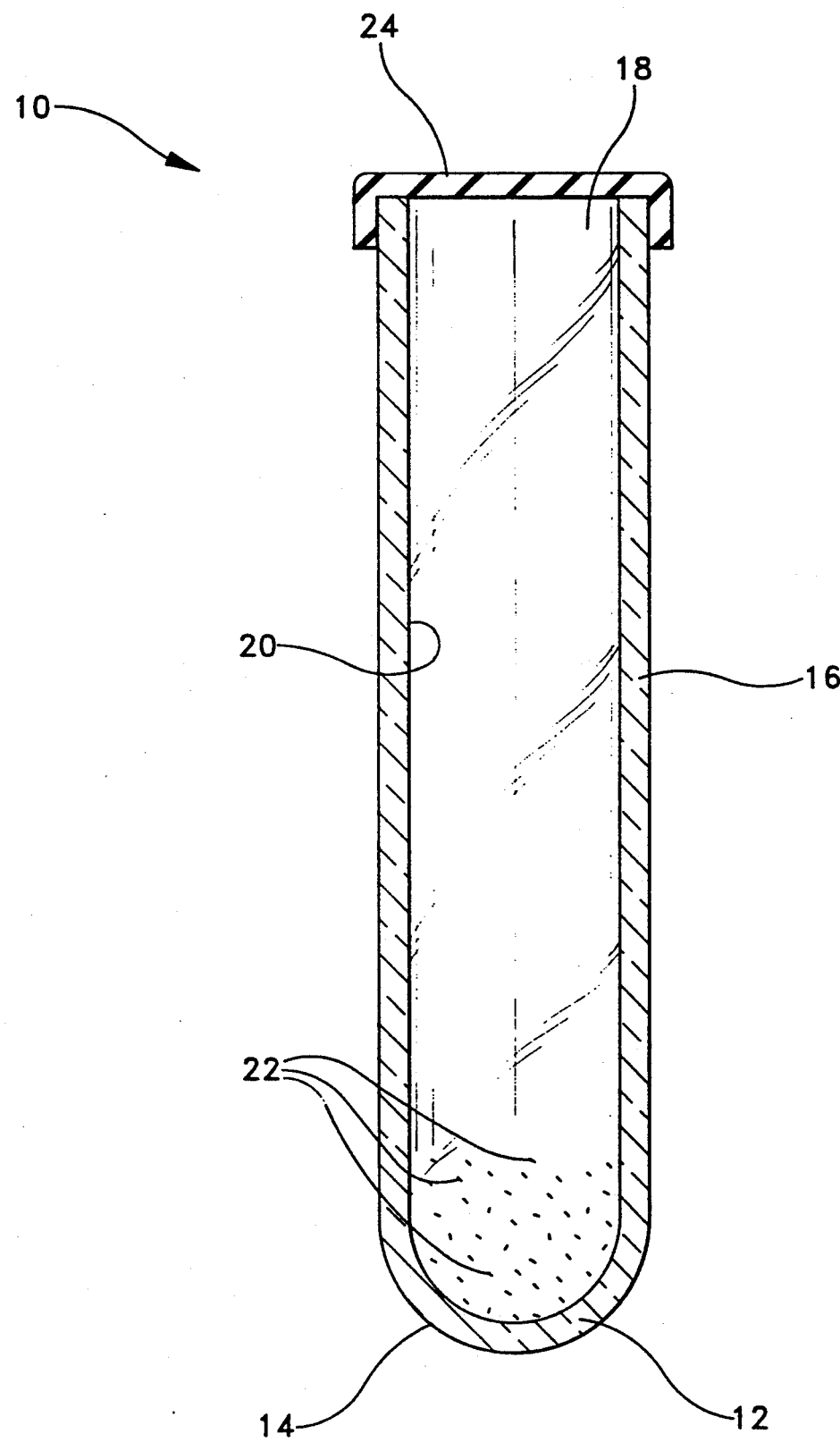
FIG. 1 is a perspective view of a blood collection assembly containing the PEC bead activator of the invention.

FIG. 1 illustrates the tube of the invention. A tube 10 has a bottom wall 12 defining a closed end 14 and a side wall 16 defining an open end 18. Bottom wall 12 and side wall 16 are continuous and together define an inside wall surface 20. A multiplicity of activating beads 22 (illustrated in detail in FIG. 2) are placed in tube 10. The open end 18 of tube 10 is covered with puncturable septum 24.

The tube may be of glass or preferably plastic. Suitable plastics are polyvinyl chloride, polypropylene, polyethylene terephthalate and preferably polystyrene (PS).

In its broadest scope, the coagulation enhancing additive of the invention contemplates a crosslinked, insoluble PEC structure having a surface charge. The surface charge may be either positive or negative, preferably negative, and the PEC structure may be of any convenient shape, preferably substantially spherical. The preferred additive is a soft and gel-like bead, but may be solid or semisolid, such as a capsule, granule, film or wire, or it may be deposited on a solid surface, such as a polymeric particle, membrane or paper.

In a first embodiment of the additive, the PEC includes a crosslinked carboxylated polymer having a surface negative charge, hereinafter referred to as the core structure. The core structure may be deposited as a film on a polymeric particle, such as a PS bead, or on a membrane such as filter paper and dried, but preferably is used in the form of the preferred gel bead.

The carboxylated polymer may be a salt of a naturally occurring anionic polysaccharide, such as alginic acid. Carboxylated polymers lacking mannuronic acid moieties may also be used. These include carboxylated polypeptides, such as a polyglutamic acid salt, a carboxylated cellulose or salts of synthetic polymers, such polyacrylic acid and polymethacrylic acid. The preferred carboxylated polymer is a salt of a carboxylated cellulose derivative such as carboxymethylcellulose (CMC). The CMC may have a molecular weight of about 5000 to 500,000, preferably about 20,000 to 100,000 most preferably about 50,000. CMC of various molecular weights is available from Hercules under the trade name AQUALON TM.

Crosslinking may be performed with a polyvalent metal ion salt such as a chloride, bromide or nitrate. Suitable metals are alkaline earth or transition group metals, such as scandium, gold, barium, magnesium or calcium. A preferred crosslinking salt is lead nitrate.

A preferred additive is a gel bead having a core structure, a plurality of polyelectrolyte layers on the core, and a negative surface charge. The core bead, which has clot-activating effect of its own, may be laminated with a plurality of layers. Thus, a CMC core bead crosslinked with a metal salt and having surface carboxylate groups may be reacted with a positively charged polyelectrolyte to add a layer over the core bead having a positive charge. This product, having a single laminated layer, is referred to as a stage 2 bead and has clot activating activity. It may be further reacted with an excess of sodium CMC or other negatively charged polyelectrolyte to add a second laminate so that the additive has a surface negative charge. One skilled in the art will readily appreciate that an additive having any desired number of laminates may be constructed by consecutive reactions using alternating positively and negatively charged polyelectrolytes.

Suitable polyelectrolytes having a positive charge are ammonium salts, salts of basic polypeptides such a polylysine and salts of aminoglycosides such as glycosaminoglycan. Preferred polycationic electrolytes are quaternary ammonium salts, such as for example, aminoethylcellulose, hexadimethrine bromide (POLYBRENE TM) and polydiallyldimethyl ammonium chloride, (poly DADMAC), available from Allied Colloids, Inc., Suffolk, Va. under the tradename ALCOFIX TM 109.

Figure 2:
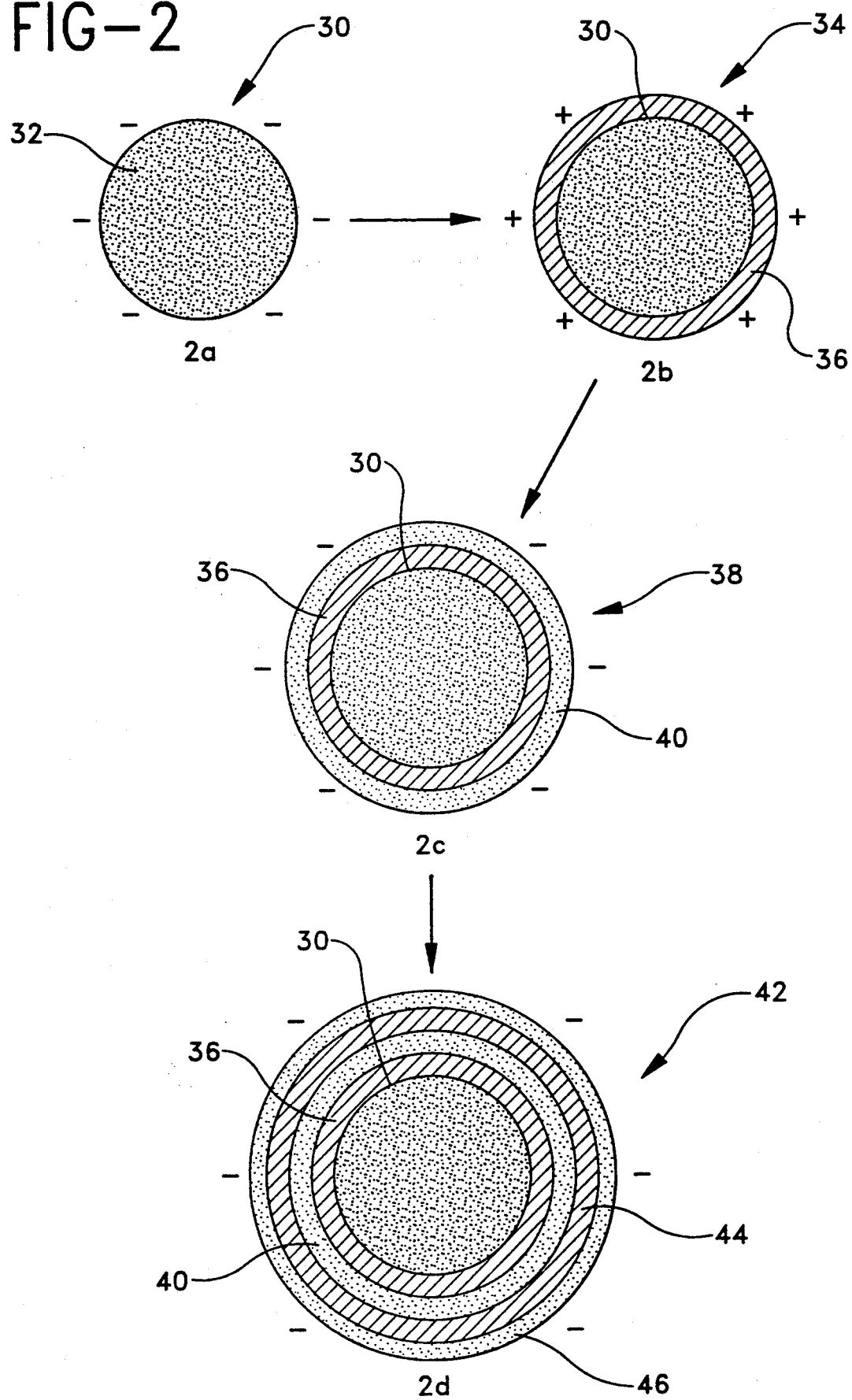
FIG. 2 illustrates various embodiments of the bead activators of the invention.

FIG. 2 illustrates various clot activating beads of the invention. The arrows in FIG. 2 show a preferred sequence of lamination reactions. FIG. 2a is a core gel bead 30 having a multiplicity of crosslinked CMC molecules 32 and a surface negative charge. Reaction of bead 30 with a positively charged polyelectrolyte, such as poly DADMAC, give a stage 2 bead 34, illustrated in FIG. 2b, which includes core bead 30 and a surface laminate 36 of poly DADMAC. FIG. 2c shows a stage 2 multilayered bead 38 having core bead 30, poly DADMAC laminate 36, and laminate 40 of CMC salt and a surface negative charge. FIG. 2d shows a stage 3 multilayered bead 42 having four laminated layers and a surface negative charge. Bead 42 includes core bead 30, laminate 36 of poly DADMAC, laminate 40 of sodium CMC, a laminate 44 of poly DADMAC and a laminate 46 of sodium CMC.

The most preferred additive of the invention includes a substantially spherical core gel bead of sodium CMC crosslinked with a divalent metal salt, a first laminate of poly DADMAC on the core bead and a second laminate of sodium CMC on the first laminate such that the final additive has a surface negative charge. This product is described in detail in Example 2 and FIG. 2c.

The additive may be about 0.01 to 10 mm, preferably about 1 to 5 mm, most preferably about 1.5 to 2.5 mm in diameter.

The core provides substantially all of the size of the beads, and the laminations do not significantly change the core size. The size of the core bead may be varied by changing the size of the orifice used in preparation of the bead and the surface tension and density of the vehicle carrier for the carboxylated polymer. Very small core beads may be prepared by dispersing the CMC in the water phase of an oil water emulsion prior to addition to the crosslinking solution. These aspects of the invention are conventional and fully understood by one skilled in the art.

The polyelectrolyte reactions described above may be performed by dropwise addition of a solution of the chosen polyanion, such as sodium CMC, to a solution of the chosen polycation, such as poly DADMAC. A double decomposition reaction takes place wherein the carboxyl groups of the CMC coordinate electrostatically with the ammonium groups of the poly DADMAC. If a net negative charge is desired on the product, an excess of carboxylate groups over ammonium groups is used. If a net positive charge is desired, the ammonium groups are present in excess. A gel-like bead of crosslinked polyanion chains forms at the interface of each drop of polyanion solution as it contacts the polycation solution. The preparation of PECs by mixing oppositely charged polyelectrolytes is well known in the art. The process is described in detail in Examples 1 and 2 and no further details are needed for a complete understanding of this aspect of the invention by one skilled in the art.

Figure 3:
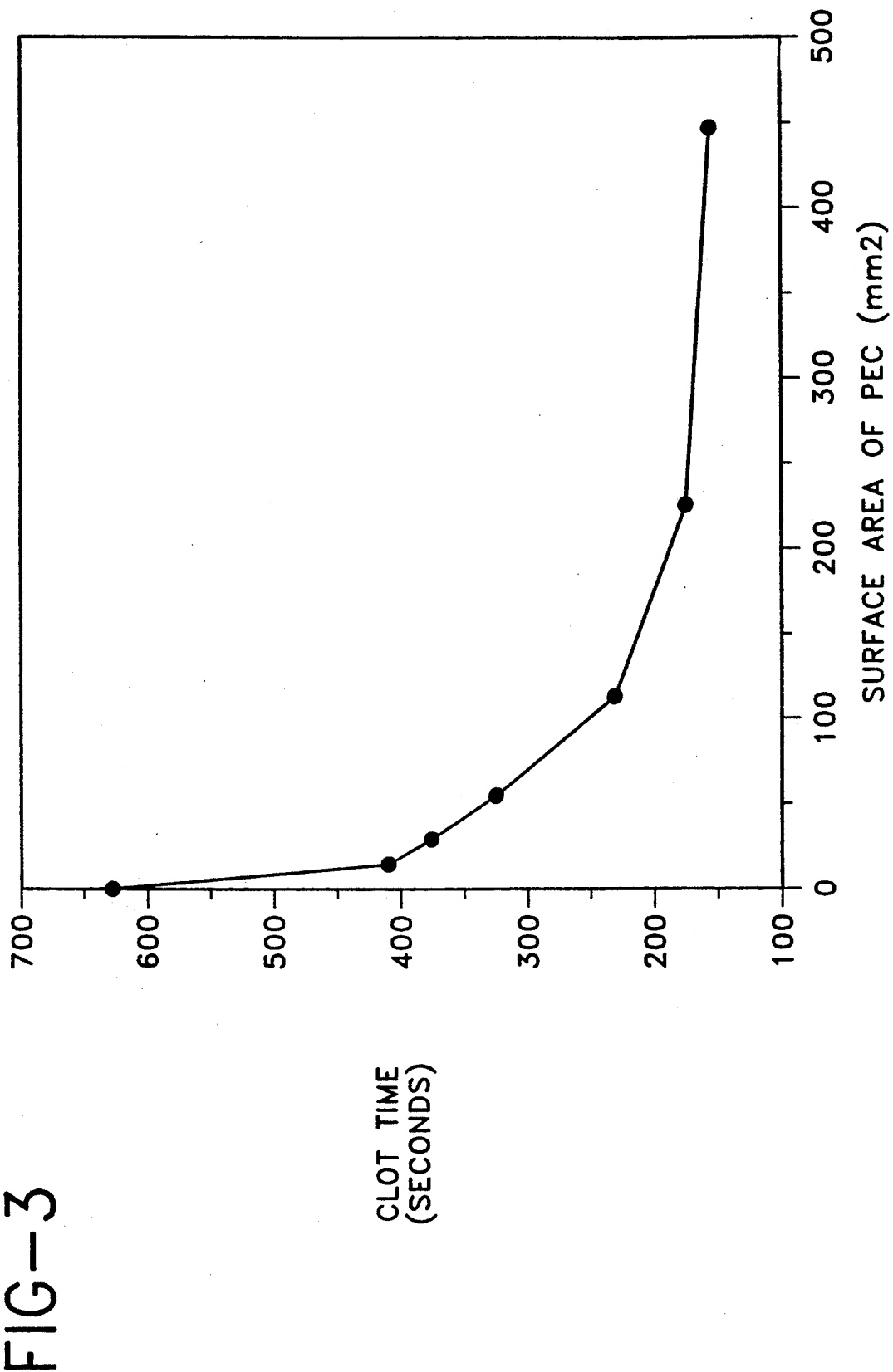
FIG. 3 is a plot of clot time against surface area for a core bead activator of the invention.

The PEC additive may be deployed into a blood collection tube in any form. The preferred gel beads may conveniently be pipetted into the bottom of a blood collection tube. Any number of beads or total surface area of beads may be used, however, clotting rate approaches an asymptote maximum as shown in FIG. 3.

EXAMPLE 1

Preparation of Core Bead

A solution of 200 ml of 0.25% by weight of sodium CMC was added dropwise with gentle stirring to 400 ml of a 0.1 molar aqueous solution of lead nitrate and the mixture was stirred gently overnight at room temperature. Beads formed at the surface and slowly sank toward the bottom of the bath. The beads were allowed to settle, then washed with deionized water by stirring for 30 min. and decanting. Washing was continued (about 4 times) until the wash solution had a final conductivity of less than 20 microsiemans. The beads comprise CMC molecules crosslinked with lead, lead carboxylate groups and free carboxyl groups. The beads are very uniform and have an average diameter of 2.11 mm. The clot activation data of these core beads was determined by the procedure of Example 5 and is given in FIG. 3.

EXAMPLE 2

Preparation of Multilayered Beads

A solution of 0.05% by weight of poly DADMAC was added to the core beads from Example 1. The mixture was stirred for about 1 hour and the poly DADMAC solution was decanted. The beads were washed 5 times with deionized water over several hours. These stage 2 beads were then treated with 0.025% by weight of sodium CMC for about ½ hour, then washed 5 times to give the preferred stage 2 multi beads of the invention. Stage 2 multi beads were then further treated consecutively with poly DADMAC and sodium CMC to give beads labeled stage 3 and stage 3 multi beads.

EXAMPLE 3

Comparison of Clot Activation by Core Beads and Multilayered Beads

Figure 4:
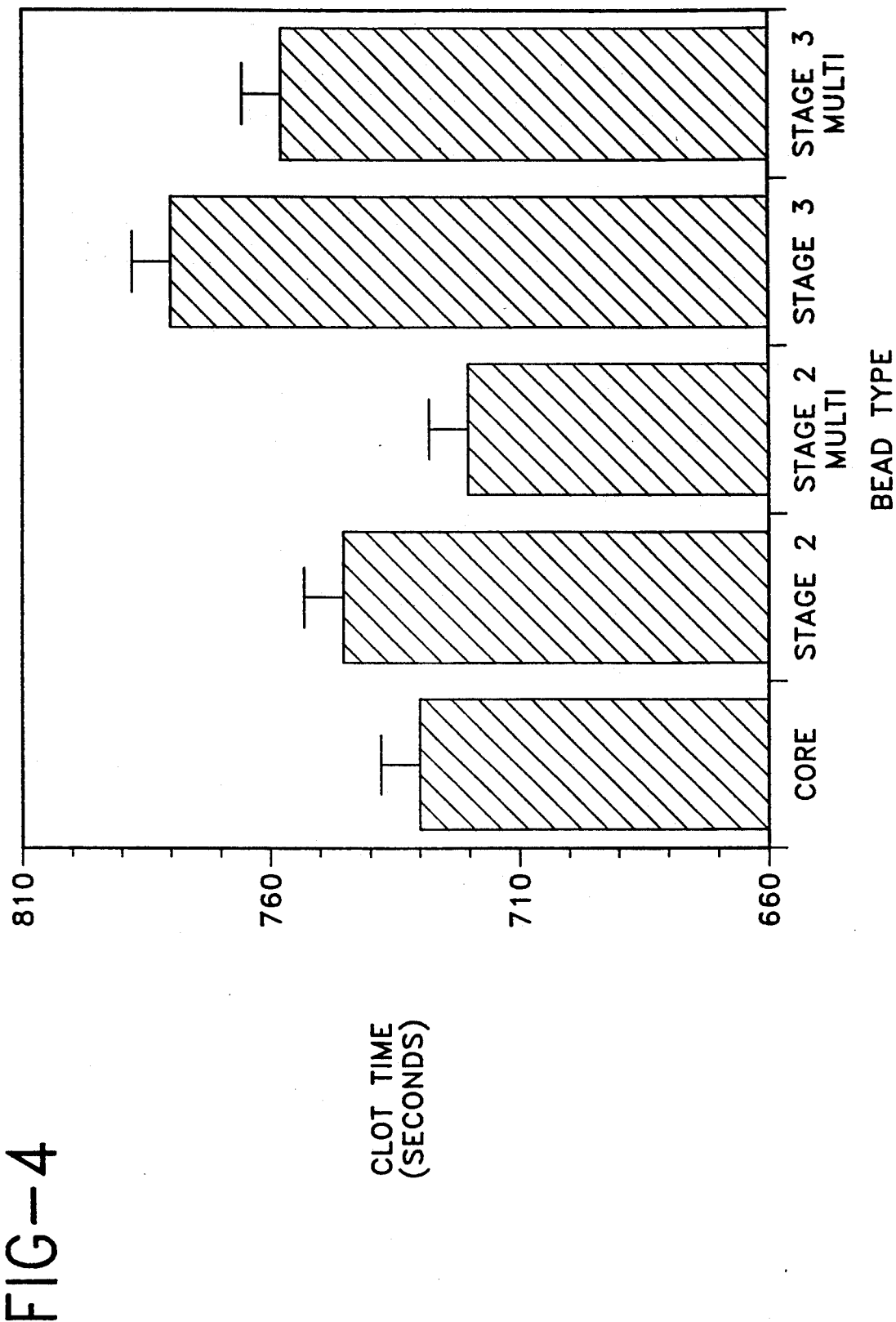
FIG. 4 is a comparison of clot times for various embodiments of the beads of the invention.

Four core beads from Example 1 and four core beads from each stage of Example 2 were tested for clot time in accordance with Example 5. The data from this experiment is given in FIG. 4. It is seen that, while the multilayered beads have a clot time somewhat higher than the core beads, the multi beads are preferred because they are more stable to mechanical shock, such as centrifuging. It is also seen from FIG. 4 that no further improvement in clot time is achieved by adding the additional layers of the stage 3 and the stage 3 multi beads.

EXAMPLE 4

Preparation of Clot Activating PEC on Filter Paper

Figure 5:
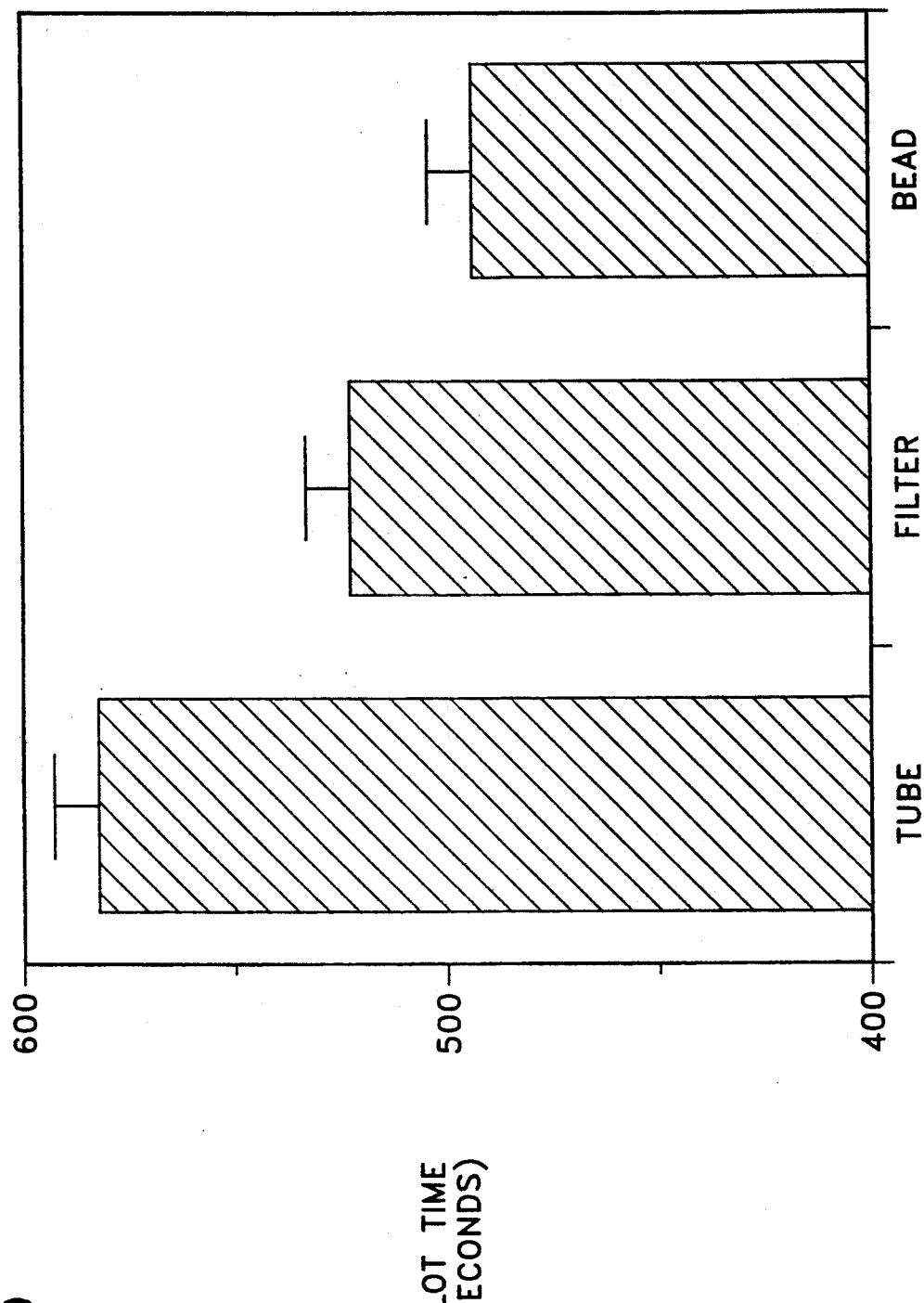
FIG. 5 compares clot activation by a PEC bead with that of a PEC deposited on a filter paper.

A piece of cellulose filter paper 2 inches×½ inch was dipped into CMC solution until saturated, then dipped into a lead nitrate bath. The paper was removed, washed, air dried, and cut into discs with a paper punch to have 56 mm² per disc. Different numbers of discs were placed in a PS tube and clot activation was determined by the procedure of Example 5. The data is presented in FIG. 5. It is seen that clotting with the filter paper PEC embodiment is faster than clotting in the tube with no activator but not as fast as occurs with the gel bead.

EXAMPLE 5

Preparation of Tubes for Coagulation Studies

Platelet poor plasma (PPP) was prepared by separating cells by centrifugation of citrated porcine blood (Environmental Diagnostics Inc.). Approximately 0.5 ml of PPP was added to PS test tubes (Becton Dickinson, 13 mm by 75 mm) containing a known number or surface area of test activator beads and the tubes were equilibrated to room temperature in a water bath for 15 minutes. Following equilibration, 200 ul of 0.2M $CaCl_2$ per ml of PPP were added to initiate coagulation. Tube contents were mixed on a laboratory inverting mixture and time of clotting noted for each tube. Clotted PPP was distinguished from nonclotted PPP by an obvious change from a fluid state to a gelatinous state which did not flow in the tube upon rotation. Clotting time was measured at this point.

What is claimed is:

1. A coagulation enhancing additive for a blood collection container comprising an insoluble polyelectrolyte complex having a surface charge, said complex comprising:
   a) a crosslinked polyelectrolyte core structure having a surface charge;
   b) a first polyelectrolyte coating on said core structure, said first coating having a surface charge opposite that of said core structure; and
   c) a second polyelectrolyte coating on said first coating, said second coating having a surface charge opposite that of said first coating, at least one of said core structure, first coating and second coating being a carboxylated polyelectrolyte devoid of mannuronic acid groups.

2. A coagulation enhancing additive for a blood collection container comprising an insoluble crosslinked carboxylated polyelectrolyte devoid of mannuronic acid groups.

3. The additive of claim 2 wherein said polyelectrolyte is a cellulose derivative.

4. The additive of claim 2 wherein said polyelectrolyte is crosslinked by a divalent or polyvalent metal ion.

5. The additive of claim 2 further comprising a coating of a positively charged polyelectrolyte on said carboxylated polyelectrolyte.

6. The additive of claim 5 further comprising a second coating of a second carboxylated polyelectrolyte on said first coating.

7. The additive of claim 5 wherein said positively charged polyelectrolyte includes an amine salt.

8. A coagulation enhancing additive for a blood collection container comprising an insoluble polyelectrolyte complex having a negative charge on its surface said complex comprising:
   a) a core structure of a first carboxylated polyelectrolyte crosslinked with a polyvalent metal ion;
   b) a first coating on said core structure, said first coating being a positively charged polyelectrolyte including an amine salt moiety;
   c) a second coating on said first coating, said second coating being a second carboxylated polyelectrolyte, at least one of said first and second carboxylated polyelectrolytes being devoid of mannuronic acid groups.

9. The additive of claim 8 wherein said first and second carboxylated polyelectrolytes are selected from the group consisting of carboxymethylcellulose, alginic acid and polyacrylic acid.

10. A blood collection assembly comprising:
    a) a blood collection container having an open end;
    b) a puncturable septum covering said open end; and
    c) an insoluble clot-enhancing additive in said container, said additive comprising an insoluble crosslinked polyelectrolyte complex having a surface charge wherein said additive is the additive of one of claims 2 and 8.

* * * * *